United States Patent [19]
Friedmann et al.

[11] Patent Number: 5,533,877
[45] Date of Patent: Jul. 9, 1996

[54] HOSE FASTENING ARRANGEMENT FOR ROLLER PUMPS

[75] Inventors: Günter Friedmann, Übersee; Helmut Wiehan, Freising; Erwin Knott, Poing, all of Germany

[73] Assignee: Stockert Instrumente GmbH, Munich, Germany

[21] Appl. No.: 388,805

[22] Filed: Feb. 15, 1995

[30] Foreign Application Priority Data

Feb. 16, 1994 [EP] European Pat. Off. ............... 94102333

[51] Int. Cl.⁶ .................................................. F04B 43/08
[52] U.S. Cl. .................................................. 417/477.1
[58] Field of Search ........................... 417/63, 477.1, 417/477.2, 474, 476, 360

[56] References Cited

U.S. PATENT DOCUMENTS

| | | | |
|---|---|---|---|
| 3,137,240 | 6/1964 | Hunt | 417/477.1 |
| 3,875,970 | 4/1975 | Fitter | 417/477 |
| 4,452,599 | 6/1984 | Albisser et al. | 604/153 |
| 4,537,561 | 8/1985 | Xanthopoulos | 417/477.2 |
| 4,573,887 | 3/1986 | Smith | 417/477.1 |
| 4,585,399 | 4/1986 | Baier | 417/477 |
| 4,599,055 | 7/1986 | Dykstra | 417/477.2 |
| 4,798,590 | 1/1989 | O'Leary et al. | 604/153 |
| 4,976,590 | 12/1990 | Baldwin | 417/53 |
| 5,062,775 | 11/1991 | Orth | 417/477.1 |
| 5,213,483 | 5/1993 | Flaherty et al. | 417/477.2 |
| 5,267,956 | 12/1993 | Beuchat | 604/153 |
| 5,433,588 | 7/1995 | Monk et al. | 417/477.2 |

FOREIGN PATENT DOCUMENTS

| | | |
|---|---|---|
| 2594496 | 9/1986 | France . |
| 3326784 | 2/1985 | Germany . |
| 1119149 | 7/1968 | United Kingdom . |
| 93/22560 | 11/1993 | WIPO . |

*Primary Examiner*—Peter Korytnyk
*Attorney, Agent, or Firm*—Scully, Scott, Murphy & Presser

[57] ABSTRACT

A hose fastening arrangement for roller pumps, especially for a heart-lung machine, which possesses a head constituted of a pump stator and pump rotor, including fastening devices for fastening of the pump piece which is inserted into the pump head of the roller pump. The hose fastening arrangement for roller pumps of the above-mentioned type is detachable from the pump head of the roller pump.

8 Claims, 2 Drawing Sheets

HOSE FASTENING ARRANGEMENT FOR ROLLER PUMPS

BACKGROUND OF THE INVENTION

1. Field of the Invention

The present invention relates to a hose attaching or fastening arrangement for roller pumps, especially for a heart-lung machine, which possesses a head constituted of a pump stator and pump rotor, including fastening devices for fastening of the pump piece which is inserted into the pump head of the roller pump.

2. Discussion of the Prior Art

Roller pumps are utilized in the medical technology, especially in heart-lung machines for the conveyance of blood in an artificial flow circuit. Basically, roller pumps consist of a pump head and a pump drive, of which, in turn, the pump head is constituted of a pump stator and a pump rotor. The pump stator is an essentially cylindrical hollow chamber wherein the inner wall thereof, which is designated as a pump bed, serves as a support for the hose piece which is inserted into the pump head and which lies against the inner wall. The pump rotor, which is rotatable about its central longitudinal axis, is arranged in the pump stator in such a manner that rollers, which are rotatably supported on a roller carrier, are rollable along the hose piece and thereby compress the hose piece. The pump stator possesses at least one opened section for conducting out of the hose, through which the hose piece is led from the internal hollow chamber of the pump stator. In order to avoid the hose piece from wandering under the influence of the rollers of the pump rotor which are rolling thereon, at least one end of the hose piece must be fastened to the pump stator. For roller pumps with reversible running directions, it is necessary to provide a fastening at both ends of the hose piece.

Because of this requirement, presently known roller pumps possess fastening devices of the most different kinds of constructional shapes; for example, clamping elements which are integrated into the pump stator and which afford a secure fastening of the hose piece.

Accordingly, it is an object of the present invention to be able to attain an improvement in the area of hose fastening for roller pumps, especially for heart-lung machines, and through the intermediary of which there is, in particular, achieved an enhanced flexibility for the hose fastening.

SUMMARY OF THE INVENTION

The foregoing object is achieved in that, pursuant to the invention, there is proposed a hose fastening arrangement for roller pumps of the above-mentioned type, which is detachable from the pump head of the roller pump.

The invention is based on the recognition that the pump stator enables itself to be divided into to parts which are clearly different with respect to their functions; namely, the pump head, which defines the properties of the pump function, and the hose fastening, which represents a retaining or holding function. Through the introduction of a hose fastening module which corresponds to this conceptual separation, and which is detachable from the pump head of the roller pump as a unit, there are achieved a plurality of advantages.

For one, through different hose fastening modules, one and the same pump head can be equipped with different retaining or holding systems for the hose piece up to the integrally connected construction. For another, sensors can be arranged in the hose fastening unit or embedded therein, which opens the possibility to be able to exchange a defective sensor through a changing of the hose fastening arrangement. In order to attach the inventive hose fastening arrangement on the pump stator, grooves are provided in the hose fastening module or in the pump stator of the roller pump, into which there are insertable protuberances and slidable therein, and which are formed on the pump stator of the roller pump or, respectively, on the hose fastening module.

With regard to the sensors which are provided in the hose fastening module, this can relate to sensors for the measurement of the properties of the medium which is conveyed by the roller pump, which are integrated into the hose fastening arrangement, for example, in the receivers which are provided therefor, or embedded in the material. Applicable sensors for this purpose, especially for heart-lung machines, offer themselves as flow-through-put measuring sensors, flow velocity sensors and bubble detectors.

Arranged in the hose fastening module are the fastening or attaching arrangements for the fastening of the hose piece which is inserted into the pump head of the roller pump. Hereby, this can relate to the internal conically-shaped receivers for external conically-shaped clamping elements. The clamping elements each possess an opening for the conducting-through of the hose, and whose diameter is slightly smaller than the diameter of the hose. The clamping elements consist essentially of two parts which are interconnected with each other in such a manner that through the insertion of the clamping element into the receiver, the hose is clamped in the opening of the clamping element due to the cooperation between the internal cone-shape of the receiver and the external cone-shape of the clamping element. The two parts of the clamping element can be connected by means of a hinge-like device, which is arranged on the clamping element in such a manner so as to cooperate with a guide groove which is provided in the receiver for effecting the orientation of the clamping element. Alternatively, there can be provided a flexible strip or film hinge for interconnecting the two parts of the clamping elements, so that it finally relates to a unitary construction. In the receiver and on the clamping element there can be formed a latching arrangement which upon the insertion of the clamping element is latchable in the receiver. In this instance, this preferably pertains to a groove extending about the internal wall of the receiver, into which there engages a bead which protrudes from and extends about the outer wall of the clamping element.

Pursuant to a modified embodiment, receivers can be provided in the hose fastening module, which are conformed to attaching members which are applied onto the hose piece. The attaching members can be formed on the hose piece and constituted of the same material as the hose piece.

According to a further embodiment, the hose piece is fixedly connected with the hose fastening module, and preferably fastened by adhesion or extrusion or injection-molding.

BRIEF DESCRIPTION OF THE DRAWINGS

The invention is now more precisely described on the basis of an exemplary embodiment, taken in conjunction with the accompanying drawings; in which.

DETAILED DESCRIPTION

Figure 1:
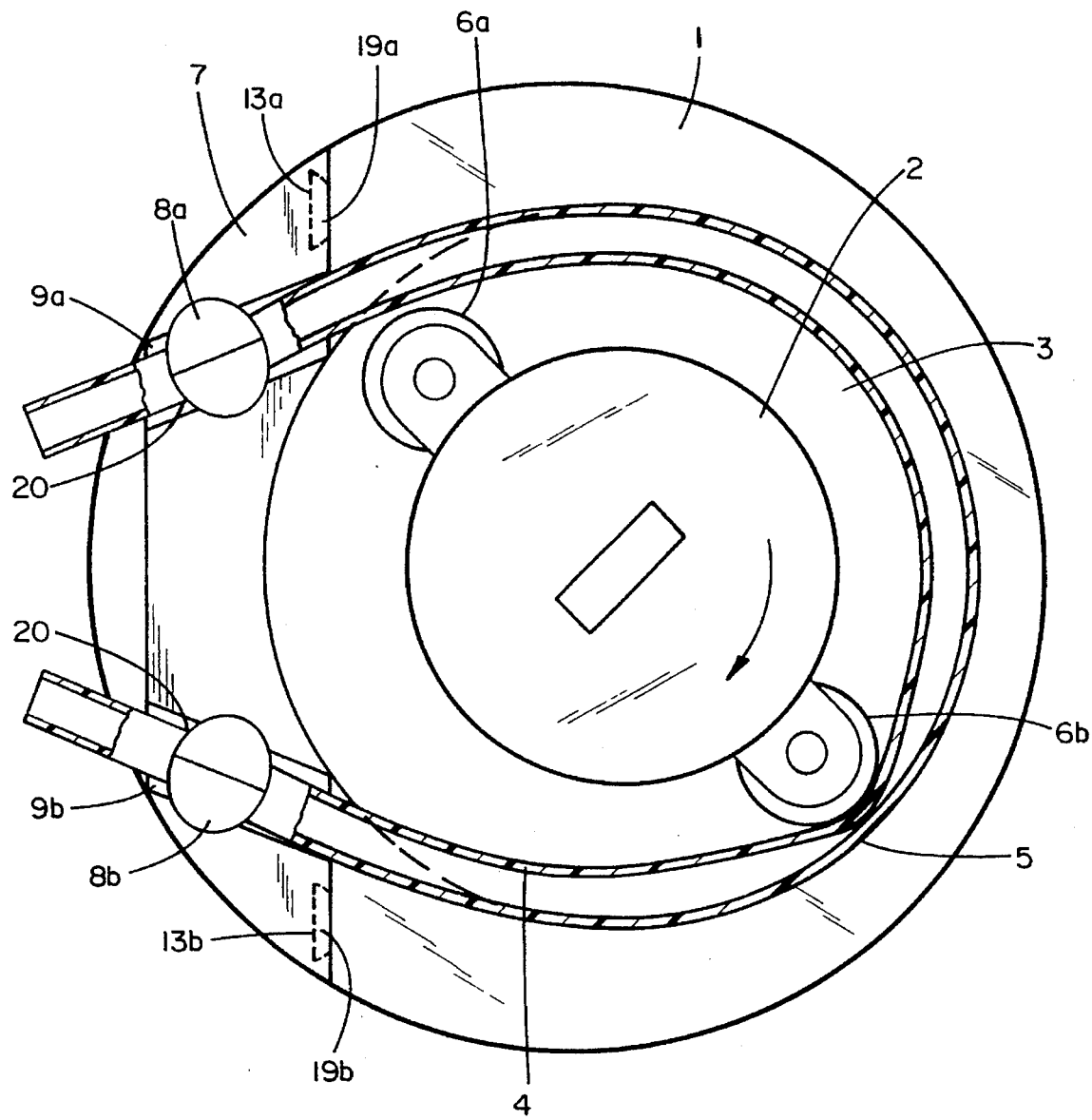
FIG. 1 illustrates an exemplary embodiment of an inventive hose fastening arrangement on the pump head of a roller pump for a heart-lung machine.

In FIG. 1 there is illustrated a roller pump which consists of a pump stator 1 and a pump rotor 2. Inserted into the essentially cylindrical hollow chamber 3 of the pump stator is a hose 4. in such a manner as to contact or lie against the inner wall 5 of the pump stator which is designated as a pump bed. The rotatably supported rollers 6a and 6b of the pump rotor roll along the hose piece and compress the latter against the inner wall 5 of the pump stator. As a result thereof, the medium which is present in the hose piece is conducted in conformance with the direction of rotation (shown by the arrow) of the pump rotor.

On the section of the pump stator 1 which is opened for the leading out of the hose piece, there is inventively arranged a hose fastening or attaching arrangement 7, which is detachable from the pump stator and resultingly from the pump head of the roller pump; in effect, although the hose fastening arrangement 7 is essentially fastened to the pump stator 1, it can, however, be detached therefrom. Two fastening devices 8a and 8b are provided in the hose fastening arrangement 7, and fixedly position the two ends of the hose piece 4 which are led out from the pump stator.

The roller pump which is equipped with the inventive hose fastening arrangement 7 does not distinguish itself with regard to its utilization from usual roller pumps. As was the case up to now, the hose piece can be inserted into the pump bed and fastened or fixed in position with the aid of the fastening arrangements 8a and 8b. However, the detachable construction of the hose fastening arrangement 7 facilitates an exchange of this module by itself, so that different fastening arrangements 8a and 8b can be employed on one and the same pump head. Furthermore, in the region of the through-passageways 9a and 9b, there can be provided sensors (not shown) which are connected with the hose fastening arrangement 7 and arranged therewith on the pump head. The sensors are preferably inserted into receivers or embedded in the hose fastening arrangement. Especially the last-mentioned embodiment facilitates an arranging of the sensors which is secure from damage and concurrently a positionally-precise locating. Should one of the sensors become defective, the hose fastening arrangement can then be separated from the pump head without any problem and thereafter replaced. An embedding of sensors in the pump stator of the roller pump is not practicable, inasmuch as with a defective sensor the entire roller pump must be disassembled in order to be able to exchange the pump stator.

Figure 2A:
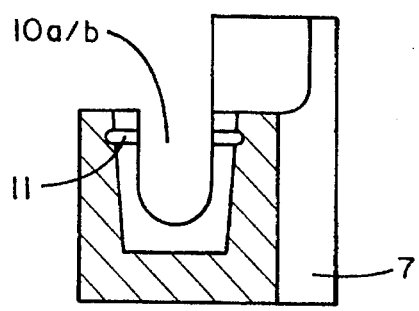
FIGS. 2A through 2C illustrate the embodiment of the hose fastening arrangement of FIG. 1 in three different views.
Figure 2B:
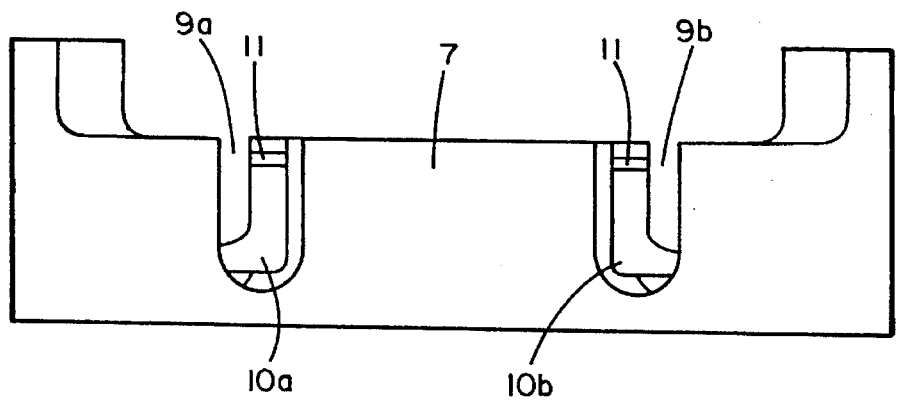
Figure 2C:
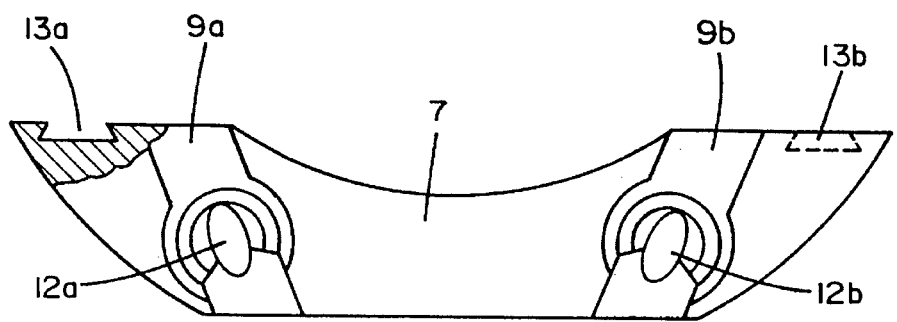

From FIGS. 2A, 2B and 2C there can be ascertained the hose fastening arrangement 7 of FIG. 1 illustrated in different views. In FIGS. 2B and 2C, there is recognizable the two passageways 9a, 9b for the two ends of the hose piece. In these passageways there are provided receivers 10a, 10b respectively for each clamping element. In FIG. 2A there is illustrated one of the receivers 10a, 10b in a cross-sectional representation. One can recognize the internal-conical configuration of the receiver and the groove 11 which is formed in and extends about the inner wall, and which represents a part of a latching device through which the clamping element is engageable in the receiver 10a, 10b. At the bottom of the receivers 10a, 10b, there are provided grooves 12a, 12b which serve for the orientation of the clamping element in the receiver, which is described in more detail in connection with the clamping element.

The hose fastening arrangement 7 possesses two grooves 13a, 13b, of which the one groove 13a is represented in a partially sectioned representation in FIG. 2C. The grooves 13a, 13b serve for the fastening of the hose fastening arrangement to the pump stator 1 (FIG. 1). Provided on the pump stator are correspondingly shaped protuberances 19a, 19b which are insertable into the grooves 13a, 13b of the hose fastening arrangement and which are slidable therein. The hose fastening arrangement 7 is attached from above onto the protuberances and lowered onto the pump stator, whereby the protuberances slide into the grooves 13a, 13b.

Figure 3:
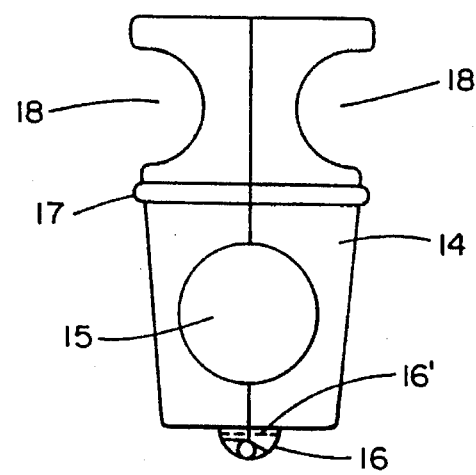
FIG. 3 illustrates an exemplary embodiment of a clamping element for the hose fastening arrangement pursuant to FIGS. 1 and 2A through 2C.

In FIG. 3 there is illustrated a clamping element 14 which can be inserted into one of the two receivers 9a, 9b (FIGS. 2A through 2C). The clamping element possesses an opening 15 having a diameter which is slightly smaller than the diameter of the hose piece, which is inserted into the roller pump. In order to be able to insert the hose piece into the opening 15 of the clamping element 14, the clamping element is divided into two parts which are pivotably interconnected by means of a hinge 16 on the lower side of the clamping element. The hinge 16 is conformed with the groove 12a, 12b (FIG. 2C) on the bottom of the receivers in such a manner, whereby an orientation of the clamping element in the respective receiver 9a, 9b is effected through the cooperation between the hinge 16 and the groove 12a, 12b. Alternatively, there can be provided a flexible strip or film hinge 16', for interconnecting the two parts of the clamping elements, so that it finally relates to a unitary construction.

Provided above the through-opening 15 is an encompassing bead 17 which, as a counterpiece to the encompassing groove 11 in the receiver 10a, 10b (FIG. 2A), represents the second part of the latching device. When the clamping element 14 together with the hose which is introduced into the through-opening 15 is inserted into one of the receivers 9a, 9b, then because of the conical shape of the clamping element and of the receiver, the hose piece is clamped into the through-opening 15. The bead 17 of the clamping element engages into the groove 11 of the receiver, and concurrently the clamping element is oriented through the cooperation between the hinge 16 and the groove 12a, 12b.

Preferably, the clamping element possesses a gripping region 18 which simplifies the insertion and withdrawal of the clamping element.

The hose fastening arrangement can be equipped with receivers in a modified embodiment, in which there are introducible the fastening members which are themselves formed on the hose piece. In addition thereto, the fastening can also be alternatively effected in that the hose piece is fixedly connected with the hose fastening arrangement, whereby in suitably configured passageways, corresponding to the passageways 9a, 9b illustrated in FIGS. 2B and 2C, the hose fastening arrangement is either adhesively fastened or attached thereabout by extrusion or injection molding.

What is claimed is:

1. A hose fastening arrangement for roller pump of a heart-lung machine, wherein a pump head is comprised of a pump stator and pump rotor, including a hose fastening means for the fastening of a hose piece which is introduced into the pump head of the roller pump, wherein grooves are provided on the hose fastening means for fastening the hose fastening means to the pump head, and protuberances are formed on the pump stator of the roller pump which are insertable into and slidable in said grooves, such that the hose fastening means is detachable from the pump head of the roller pump.

2. A hose fastening arrangement according to claim 1, wherein the hose piece is fixedly connected with the hose fastening means.

3. A hose fastening arrangement according to claim 2, wherein the hose piece is adhesively attached to the hose fastening means.

4. A hose fastening arrangement for a roller pump of a heart-lung machine, wherein a pump head is comprised of a pump stator and a pump rotor, and including a hose fastening means for fastening a hose piece which is introduced into the pump head of the roller pump, and the hose fastening means is detachable from the pump head of the roller pump, wherein internal conical recievers are provided for external conical clamping elements, with each clamping elements comprising at least two parts and having an opening for the through-passage of a hose, with diameter of the opening being smaller than the diameter of the hose, and at least two parts of each clamping element being interconnected, such that upon the insertion off a clamping element into a receiver, the hose is clamped in the opening of the clamping element because of contact of the internal cone of the receiver with external cone of the clamping element.

5. A hose fastening arrangement according to claim 4, wherein the least two parts of each clamping element are interconnected by a hinge-like device arranged on the clamping element which fits into a guide groove provided in the receiver for orienting the clamping element in the receiver.

6. A hose fastening arrangement according to claim 4, wherein a film hinge interconnects the at least two parts of each clamping element.

7. A hose fastening arrangement according to claim 6, wherein the film hinge is intergrally constructed with the at least two parts of the clamping element.

8. A hose fastening arrangement according to claim 4, wherein a latching means is formed on each receiver and on each clamping element, which latching means are engageable when the clamping element is inserted into the receiver.

* * * * *